(12) United States Patent
Popescu

(10) Patent No.: US 9,706,971 B2
(45) Date of Patent: Jul. 18, 2017

(54) METHOD AND X-RAY SYSTEM FOR DUAL-ENERGY SPECTRA CT SCANNING AND IMAGE RECONSTRUCTION

(71) Applicant: Siemens Aktiengesellschaft, Munich (DE)

(72) Inventor: Stefan Popescu, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 290 days.

(21) Appl. No.: 14/468,436

(22) Filed: Aug. 26, 2014

(65) Prior Publication Data
US 2015/0071400 A1   Mar. 12, 2015

(30) Foreign Application Priority Data
Sep. 6, 2013 (DE) .......................... 10 2013 217 852

(51) Int. Cl.
*A61B 6/00*  (2006.01)
*G01N 23/04* (2006.01)
(Continued)

(52) U.S. Cl.
CPC ............ *A61B 6/5235* (2013.01); *A61B 6/482* (2013.01); *A61B 6/502* (2013.01); *A61B 6/5205* (2013.01);
(Continued)

(58) Field of Classification Search
CPC .... G01N 23/046; A61B 6/032; A61B 6/5235; A61B 6/482; A61B 6/502; A61B 6/5205; G06T 2211/408; G06T 2211/421
(Continued)

(56) References Cited

U.S. PATENT DOCUMENTS 7,209,537 B2    4/2007   Popescu
2006/0109951 A1  5/2006   Popescu
(Continued)

FOREIGN PATENT DOCUMENTS

CN     1765327 A     5/2006
CN     102151140 A   8/2011
(Continued)

OTHER PUBLICATIONS

Guang-Hong Chen et al., "Prior image constrained compressed sensing (PICCS): A method to accurately reconstruct dynamic CT imgages from highly undersampled projection data sets", Med. Phys., vol. 35, No. 2, pp. 660-663, Feb. 2008; Feb. 1, 2008.
(Continued)

*Primary Examiner* — Courtney Thomas
(74) *Attorney, Agent, or Firm* — Harness, Dickey & Pierce, P.L.C.

(57) ABSTRACT

A method for dual-energy spectra CT scanning and image reconstruction of two tomographic image datasets from a higher-energy and a lower-energy x-ray energy spectrum is disclosed. In at least one embodiment, readings are taken with the different x-ray energy spectra during the scanning; the different x-ray energy spectra are also created at least by different acceleration voltages of the x-ray source; and the spatial distribution of the scanning x-rays per x-ray energy spectrum is undertaken randomly or pseudo-randomly (in the absence of a regular pattern). With the attenuation datasets thus obtained, reconstructions of two tomographic image datasets in accordance with a least one iterative CS reconstruction method are carried out and subsequently the reconstructed tomographic image datasets are stored and/or output and/or further processed.

28 Claims, 9 Drawing Sheets

(51) Int. Cl.
*G06T 11/00* (2006.01)
*A61B 6/03* (2006.01)

(52) U.S. Cl.
CPC .......... *G01N 23/046* (2013.01); *G06T 11/006* (2013.01); *A61B 6/032* (2013.01); *G01N 2223/423* (2013.01); *G06T 2211/408* (2013.01); *G06T 2211/424* (2013.01)

(58) Field of Classification Search
USPC ....................................................... 378/4–20
See application file for complete search history.

(56) References Cited

U.S. PATENT DOCUMENTS

2012/0314835 A1   12/2012  Muller
2013/0083886 A1*  4/2013  Carmi .................. G06T 11/006
                                                        378/16
2013/0308745 A1*  11/2013  Goshen ................ G06T 11/005
                                                        378/5

FOREIGN PATENT DOCUMENTS

CN        102711622 A    10/2012
WO    WO 2012104740 A1    8/2012

OTHER PUBLICATIONS

Aybat N.S. et al., "Fast Reconstruction of CT Images from Parsimonious Angular Measurements Via Compressed Sensing", pp. 1-31.

* cited by examiner

METHOD AND X-RAY SYSTEM FOR DUAL-ENERGY SPECTRA CT SCANNING AND IMAGE RECONSTRUCTION

PRIORITY STATEMENT

The present application hereby claims priority under 35 U.S.C. §119 to German patent application number DE 10 2013 217 852.2 filed Sep. 6, 2013, the entire contents of which are hereby incorporated herein by reference.

FIELD

At least one embodiment of the invention generally relates to a method and/or an x-ray system for dual-energy spectra CT scanning and image reconstruction of two tomographic image datasets from a higher-energy and a lower-energy x-ray energy spectrum.

BACKGROUND

Diverse methods are known in the prior art for scanning an examination object with two or more different x-ray energy spectra.

In a first simple variant a single-energy source x-ray system is used, which carries out two object scans serially one after the other with different energy spectra, wherein each scan comprises at least one half orbit and a different acceleration voltage is set at the x-ray tube in each case. This method proves problematic however, especially for the scanning of patients, since spatial shifts can occur between the scans and thus a strict spatial correlation is no longer to be insured between the individually determined object data.

A dual-energy source x-ray system is also mostly used for dual-energy spectra scanning, which scans the examination object temporally in parallel with the aid of two x-ray tubes operated with different acceleration voltages and thus delivers two projection datasets per x-ray energy spectrum, from which the image datasets can then be reconstructed. In practice, on grounds of cost, detectors with different spatial extent are used in such dual-energy source x-ray systems, so that one of the datasets is based on a smaller measurement field and corresponding restrictions in the datasets obtained therefrom must be accepted.

As an alternative, scanning methods are also known in which, with the aid of a fast switching of the acceleration voltage using a single mobile emitter-detector arrangement (fast-kV-switching) between the individual readings, temporally parallel projection datasets are determined with different x-ray energies and image datasets are reconstructed therefrom in each case. The problem in such cases is that, while retaining an unchanged tube current independent of the acceleration voltage, drastically different photon flows arise as a function of the acceleration voltage, so that correspondingly drastically different signal-to-noise ratios are also produced in the image data calculated therefrom. In order to solve this problem it has also been proposed that the tube current be changed accordingly for each reading, so that largely the same dose product of tube current IR, scan time t and acceleration voltage $URk$ is produced, wherein the exponent k is selected such that, under the given conditions (pre-filter, anode material, irradiation geometry, etc.), the signal-to-noise ratio (SNR) produced is equal to the measurements at both acceleration voltages. However relatively complex power supplies and cathode constructions, which allow a correspondingly rapid modulation of the tube current, are needed for this purpose.

To avoid a tube current modulation and to achieve a largely equal dose product despite this, it is proposed, in a further variant of the fast-kV-switching method in publication U.S. Pat. No. 7,209,537, with the distribution of the readings and the reading time remaining the same, that the switch-on time of the two different acceleration voltages be varied so that the higher voltage (here 140 kV) amounts to only 20% of the switch-on time of the lower voltage (here 80 kV) related to each reading. Thus the same dose product is produced for the said acceleration voltages, taking into account the evenly distributed and alternating readings with higher and lower acceleration voltage for each acceleration voltage. However equipping the device in a way that allows a very fast switchover of the acceleration voltages is also necessary here. In addition a part of the reading time with high acceleration time is not needed for irradiation, so that a lengthening of the scanning time is produced.

Furthermore new iterative reconstruction methods are known in the prior art with which projection data obtained by stochastic scans can be used for reconstruction, such stochastic scans also being described in literature by the term "sparse sensing", i.e. compressible or incomplete or sparse or sparsely-populated scanning. Basically in this iterative reconstruction method a distinction is made between a "compressed sensing (=CS)" reconstruction and a "prior-image constrained compressed sensing (=PICCS)" reconstruction, a reconstruction constrained by a previously known image after compressed sensing. As regards CS reconstruction, reference is made to the article entitled "FAST RECONSTRUCTION OF CT IMAGES FROM PARSIMONIOUS ANGULAR MEASUREMENTS VIA COMPRESSED SENSING" by N. S. AYBAT AND A. CHAKRABORTY. In relation to the PICCS reconstruction the publication "Prior image constrained compressed sensing (PICCS): A method to accurately reconstruct dynamic CT images from highly undersampled projection data sets" Guang-Hong Chen, a Jie Tang, and Shuai Leng, Med Phys. 2008 February; 35(2): 660-663, is cited as an example.

While CS reconstruction is undertaken exclusively with the stochastically-determined scanning data, the PICCS reconstruction uses the image information of a preceding image (prior image) of the examination object in addition to the stochastic scanning data.

To define the various technical terms rendered in German in the original we would like to state that the German term "Zwei-Energiespektren" is used in the original German document for the generally known English term "Dual-Energy", for example in conjunction with Dual-Energy-CT or Dual-Energy-CT scanning. Furthermore English technical terms have been rendered in the original German document by the following German terms:
Single-Source=Ein-Strahlenquelle;
Dual-Source=Zwei-Strahlenquellen;
Reading=Auslesung and
Prior image=Vor-Bild.

In addition, the literal translation "komprimierte Abtastung" has been used for the English technical term "compressed sensing", for which no suitable German technical term has been established at present, wherein it is pointed out that although this corresponds to a word-for-word translation, its sense does not correspond to the English technical term "compressed sensing".

SUMMARY

At least one embodiment of the invention is directed to an improved method and/or an improved x-ray system for dual-energy spectra CT scanning with two different x-ray energy spectra and image reconstruction of two tomographic image datasets on the basis of the different x-ray energy spectra.

Advantageous developments of the invention are the subject matter of dependent claims.

A method is disclosed for dual-energy spectra CT sampling and image reconstruction of two tomographic image datasets from a high-energy and a low-energy x-ray energy spectrum, the method comprising:

scanning an examination object with an x-ray source from a plurality of projection positions and projection directions with two different x-ray energy spectra and determination in each case of an undersampled attenuation dataset of the examination object for each x-ray energy spectrum, wherein:

the different x-ray energy spectra are at least also created by different acceleration voltages of the x-ray source and the spatial distribution of the sampling x-rays is undertaken randomly or pseudo-randomly, reconstruction of two tomographic image datasets using the two undersampled attenuation datasets in accordance with at least one iterative compressed sampling method, and storage and/or output and/or further processing of the reconstructed tomographic image datasets.

In addition to the embodiments of the method described here for scanning and reconstruction, the scope of the invention also includes an embodiment of an x-ray system for creating tomographic image data, comprising:

at least one emitter-detector system which, during a scanning period, can determine projection data with a predefined x-ray energy spectrum in each case from a plurality of projection positions and projection directions, a computer system for controlling the at least one emitter-detector system and evaluating determined projection data for reconstructed tomographic image datasets, and a memory for storing computer programs which are executed by the computer system during operation, wherein at least one computer program is stored in the memory, which during operation can execute at least one of the variants of the inventive method described here.

BRIEF DESCRIPTION OF THE DRAWINGS

The invention is described below in greater detail on the basis of the preferred example embodiments with the aid of the figures, wherein only the features necessary for understanding the invention are presented. The following reference characters are used: 1: Single-energy source/C-arm system/mammography tomosynthesis system; 2: X-ray tubes; 3: Detector; 4, 5: Pressure plate; 6: Gantry/C-arm/Pivot arm; 7: Patient; 8: Patient table; 9: System axis; 10: Control and processing system/computer system; CS: Compressed sensing (incomplete sampling); FBPR: Filtered back projection reconstruction; HE: Higher-energy x-ray energy spectrum: LE: Lower-energy x-ray energy spectrum; iCSR: Iterative CS reconstruction; IR: Tube current; Prg1-Prgn: Computer programs; S1-S6, Spi: Method steps; t: Time; UR: Acceleration voltage.

In the individual figures.

DETAILED DESCRIPTION OF THE EXAMPLE EMBODIMENTS

Figure 1:
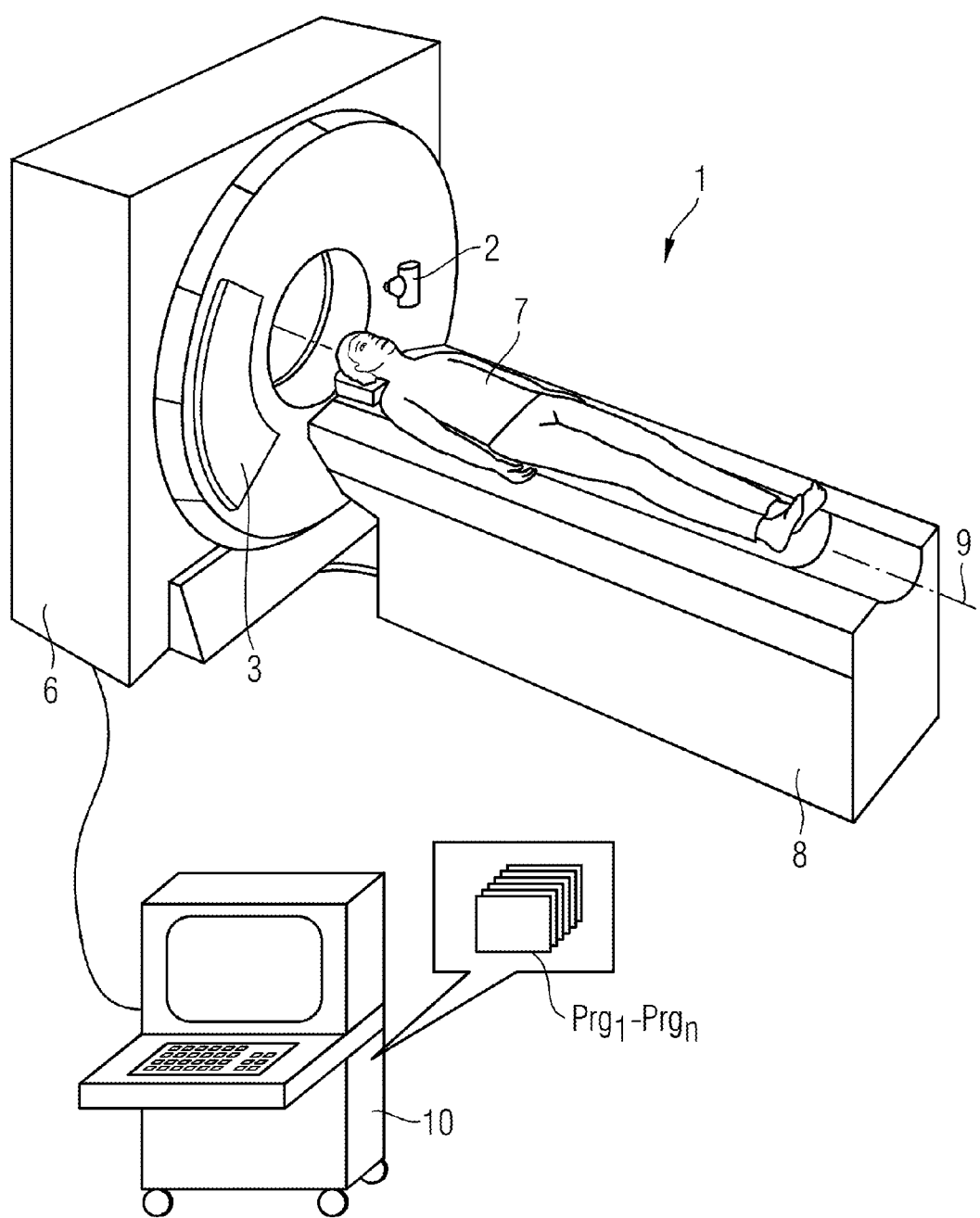
FIG. 1 shows an x-ray source CT system.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The inventor has recognized that it is possible, with a single emitter-detector system, to carry out dual-energy spectra scans in which a dose distribution equilibrium between the higher and the lower-energy x-ray spectrum is achieved without having to influence the tube current and without needing especially fast-switching power supplies for the acceleration voltage of the x-ray tubes. In this case it is sufficient for the power supply to be capable, from one reading to the other, of switching the acceleration voltage between the voltage values used, wherein the duration of the presence of the acceleration voltage per reading can be the same for the low and the high acceleration voltage.

This is achieved on the one hand by periods of the same length always being used for each reading for the application of the acceleration voltage selected in each case and simultaneously however by a corresponding choice of the ratio of the number of readings of the acceleration voltages used, it being insured that overall, with the acceleration voltages used, a largely equal photon flow or an equally large dose product is used for measurement. In addition an even pattern may not be used for this distribution of the readings of various voltages, but a random distribution of the readings with the predetermined ratio in accordance with the dose product must occur. Since at the same time each reading is to be needed for one pass and on the other hand no reading can be occupied by more than one acceleration voltage, the readings should also proceed in a complementary manner to one another and should supplement one another without gaps overall.

Because of the widely differing dose product with the same tube current with different acceleration voltages, widely differing reading numbers for the acceleration voltages used are accordingly produced. If the dose products of the acceleration voltages 140 kV, 120 kV and 80 kV are considered in relation to one another with the same tube current, the 140 kV radiation produces 100%, the 120 kV radiation 40% and the 80 kV radiation produces just 20% of the dose product. This thus means that for example, with the parallel use of two acceleration voltages or x-ray energy spectra respectively with 140 kV and 80 kV, for achieving the same dose product the 140 kV readings may only amount in numerical terms to a fifth of the 80 kV readings. Related to a typical pass of a CT emitter-detector system with 1152 readings, 960 readings are then assigned to the 80 kV acceleration voltage and only 192 readings to the 140 kV acceleration voltage. In the event of the two acceleration voltages 120 kV and 80 kV being used, the ratio of the readings for 120 kV to 80 kV would be equal to 1 to 2, i.e. 384 to 768 per pass.

To achieve a good image quality in the reconstruction of image data from such undersamplings, it is proposed in accordance with the invention that an iterative reconstruction method be used which takes account of the undersampling, wherein it is however necessary for the undersampling not to take place regularly or according to a repeating pattern but in a stochastic or quasi-stochastic way. At least for the reconstruction of the at least one image dataset of an x-ray energy spectrum, preferably of the low-energy spectrum, it is proposed that the iterative CS reconstruction method be used in which the optimization of the cost problem $$\hat{x} = \underset{x>0}{\operatorname{argmin}}\{L(Ax, y) + \beta \cdot \|\Psi(x)\|_1\}$$

is an objective, wherein $L(Ax,y)=(y-Ax)^T W(y-Ax)$ corresponds to the data fidelity term and $\|\Psi(x)\|_1$ to the sparsity enforcing term. In this case the variables used refer to the following:
A=forward projection matrix,
L=geometrical norm,
T=transposition operator,
W=noise weighting matrix,
$\hat{x}$=sought value of the image matrix,
x=image matrix values of the current iteration,
y=measured values,
β=regularization factor and
$\|\Psi(x)\|_1 = L_1$ norm.

If the number of readings is very small however, the iterative PICCS reconstruction method can be used up to an undersampling factor of ≥20. Thus if the ratio of the readings of high to low-energy sampling is shifted drastically in one direction of the readings then, taking into account that both samplings describe the same object and therefore great similarity is present, initially an iterative CS reconstruction with the projection data of the more frequent sampling rate can be carried out, the result image defined as a prior image and then a PICCS reconstruction carried out with the projection data of the relatively sparse sampling rate using the prior image previously obtained.

For the execution of the iterative PICCS reconstruction the optimization of the cost problem $$\hat{x} = \underset{x>0}{\operatorname{argmin}}\{L(Ax_{HE}, y_{HE}) + \beta \cdot \|\Psi(x_{HE} - x_{LE})\|_1 + (1-\beta) \cdot \|\Psi(x_{HE})\|_1\}$$

is to be resolved, wherein here too $L(Ax_{HE}, y_{HE})=(y_{HE}-Ax_{HE})^T W(y_{HE}-Ax_{HE})$ corresponds to the data fidelity term and $\|\Psi(x)\|_1$ to the sparsity enforcing term. The variables used have the same meanings as in the CS reconstruction, wherein HE represents the index of the data from the higher-energy or sparse sampling and LE the index of the data from the lower-energy and thus also more frequent sampling.

As an alternative a combination of the two iterative reconstruction methods for creating tomographic image data can be carried out with preferably the lower-energy and the higher-energy sampling, in that for the two samplings initially an iterative CS reconstruction is carried out, wherein its result is used in each case in a subsequently performed iterative PICCS reconstruction as prior image for the respective other sampling. In this way the sampling information present alternately is used and information gaps which arise as a result of the incomplete sampling with the respective energy spectrum are largely compensated for, wherein however the focus remains on the actual projection dataset being observed.

A further alternative variant of an embodiment of the inventive method includes the determined projection data from both x-ray energy spectra initially being combined to a mutually-supplementing and thus complete projection dataset subsequent to the inventive dual-energy spectra scanning of the examination object. With this complete projection dataset a conservative reconstruction calculation for example an FBP (filtered back projection) reconstruction for a tomographic image dataset can be carried out, which is subsequently considered as a prior image. Then this prior image is included for the CS reconstruction and/or PICCS reconstruction, with which the tomographic image data is then calculated for one of the x-ray energies in each case.

Although at least one embodiment of the invention basically relates to dual-energy spectra scanning with a single emitter-detector system, preferably in a CT system, a C-arm system or a mammography system, the method can also be used in conjunction with a corresponding dual-energy source system. In this case either the emitter-detector system present there and the emitter-detector system-specific sampling datasets produced therefrom can each be considered and used in isolation. As an alternative however the datasets thus obtained can be mixed or combined.

For example, with the use of two emitter-detector systems with the same acceleration voltage pair, the projection data obtained can be combined such that the scanning time is significantly shortened. The advantage of such a method of operation lies in the fact that the measurement field of the dual-energy spectra measurement, even with detectors of different sizes, is no longer restricted to the smaller detector, but corresponds to the larger of the two detectors used.

On the other hand, with a dual-energy source system, the one emitter-detector system can be entirely operated with an acceleration voltage U1, while the other emitter-detector system is operated with two different, preferably higher acceleration voltages U2 and U3, which are switched over stochastically or quasi-stochastically. In this case, in accordance with the voltage used, it can be insured that the number of readings of the individual voltages, with the tube current remaining the same, is distributed so that the dose products of all voltages U1 to U3 are largely equal. The tube currents remaining the same for each emitter-detector system can be selected differently here to match the dose lines. It would be advantageous here for only the power supply of one of the emitter-detector systems to be adapted and the prior image could also be calculated with a standard FBP reconstruction.

In accordance with the basic idea set out above, the inventor proposes, in at least one embodiment, the following:

A method is disclosed for dual-energy spectra CT sampling and image reconstruction of two tomographic image datasets from a high-energy and a low-energy x-ray energy spectrum, the method comprising:

scanning an examination object with an x-ray source from a plurality of projection positions and projection directions with two different x-ray energy spectra and determination in each case of an undersampled attenuation dataset of the examination object for each x-ray energy spectrum, wherein:

the different x-ray energy spectra are at least also created by different acceleration voltages of the x-ray source and the spatial distribution of the sampling x-rays is undertaken randomly or pseudo-randomly, reconstruction of two tomographic image datasets using the two undersampled attenuation datasets in accordance with at least one iterative compressed sampling method, and storage and/or output and/or further processing of the reconstructed tomographic image datasets.

It is pointed out that the term random or pseudo-random is essentially intended to describe that the sampling is undertaken without a regular pattern which would lead to artifacts in a CS or PICCS reconstruction. Such types of sampling can be achieved not only by actual random patterns of the sampling but also by the use of predetermined sampling sequences which are based on a random and non-regular specification.

In an advantageous embodiment variant of the inventive method it is proposed that the sampling be undertaken such that the sum of the sampling x-rays of all x-ray energies used produces a regular sampling pattern. Thus, although based on one x-ray energy spectrum in each case, a random, i.e. non-regular and non-pattern-based sampling pattern is selected, so that thus no artifacts arise in the later reconstruction. If however the totality of the samplings with all x-ray energies used is considered, then a regular sampling pattern with a plurality of readings of equal length and radiation times of equal length per reading is produced. Accordingly this also means that the sampling occurs such that the x-rays of two different x-ray energies are disposed complementarily to one another, i.e. supplement each other spatially and temporally without redundancy.

It is further advantageous for the acceleration voltage to be controlled such that the accumulated sampling time with the higher x-ray energy spectrum is smaller than with the lower x-ray energy spectrum, especially that the ratio of the accumulated sampling time with the higher x-ray energy spectrum and the accumulated sampling time with the lower x-ray energy spectrum is determined such that the two samplings are undertaken with an overall equal photon energy deposition in the detector or with the same dose product respectively. The dose product in this case is calculated with the formula $DM=IR*t*UR^k$, wherein DM is the average dose product, IR is the tube current of the x-ray tubes used, UR is the acceleration voltage of the x-ray tubes, and t is the radiation time and k is selected so that, regardless of the acceleration voltage and the tube current, the measured signal-to-noise ratios (SNR) in the detector are the same for the higher and the lower x-ray energy spectrum. Here in accordance with the invention the acceleration voltage selected in each case for one reading can be present with the same length independently of the size of the acceleration voltage while the tube current remains constant. The value k, with conventional CT systems, mostly ranges between 2 to 3, for example at 2.87 for a current CT system of the applicant. Basically this value is for example dependent on the pre-filter used and the anode material used, so that it should be defined individually for each type and version of a CT system.

It is further proposed in an embodiment variant that the reconstruction of both tomographic datasets be undertaken independently of one another and in accordance with the same iterative CS reconstruction method. This method is especially preferred if the respective sums of the readings for each x-ray energy or acceleration voltage respectively do not differ too drastically. This is especially applicable if the acceleration voltages also lie relatively close to one another, i.e. for example in the use of a first acceleration voltage of approximately 80 kV and the second acceleration voltage of approximately 120 kV. Here the same dose product or the same photon flow respectively is achieved if the ratio of the overall irradiation times to one another is around 1 to 2, corresponding to the same photon flow, the same signal-to-noise ratio is then also produced in the reconstructed image data.

In another embodiment variant, the inventor proposes that initially the reconstruction of the lower-energy, tomographic dataset is undertaken in accordance with the iterative "first" CS reconstruction method and then the higher-energy tomographic dataset is reconstructed with the inclusion of the reconstructed low-energy tomographic dataset as prior image in accordance with the PICCS reconstruction method. Since the PICCS reconstruction method is to be applied especially usefully if the sampling is only undertaken very sparsely, this method is particularly useful when the acceleration voltages used lie relatively far from one another, for example if 80 kV is used as the first and the 140 kV or higher is used as the second acceleration voltage. To achieve the same dose product reading ratios of 1 to at least 5 are produced here, so that with the higher acceleration voltage only relatively few readings are present. By the use of the additional information from the prior image of the lower x-ray energy spectrum the present information deficits can thus largely be compensated for in advantageous manner.

Finally it is also proposed in a third embodiment variant of the inventive method that initially a reconstruction of higher and lower-energy tomographic datasets independently of one another and in accordance with the same iterative CS reconstruction method is undertaken and subsequently, for each x-ray energy spectrum, an iterative PICCS reconstruction method is applied, wherein the tomographic datasets determined in accordance with the CS reconstruction are used for the other x-ray energy in each case as a prior image in a subsequent iterative PICCS reconstruction method. In such a combined use of image data already reconstructed beforehand with the other energy spectrum in each case, sampling information already present from the respective other x-ray spectrum is also used for both energy spectra in the reconstruction and where possible information gaps caused by non-available samplings are filled. The disadvantage however is that the computing effort overall is relatively high.

At least one embodiment of the inventive method can especially preferably be carried out by a single-energy source CT system, a C-arm system, or a mammography tomosynthesis system. Naturally the single-energy source CT system initially cited also relates to mammography systems which operate in accordance with the principle of an emitter-detector system rotating in an orbital shape. The mammography tomosynthesis system relates to systems in which the emitter, mostly with a stationary detector, is only pivoted over a predetermined angular range of less than or equal to 180°.

The scope of the invention also includes the previously described embodiments of the method when it is applied to a dual-energy source CT system, wherein the two emitter-detector systems present there can be considered in each case as a single-source energy system per se in each case. As an alternative, samplings from the two emitter-detector systems used can be combined with one another in any given way in order to carry out embodiments of the method described above.

The scanning and reconstruction method described here is suitable both for the scanning of the examination object as a spiral scan and also for the scanning of the examination object as an orbital scan, preferably as a sequential orbital scan.

In addition to the embodiments of the method described here for scanning and reconstruction, the scope of the invention also includes an embodiment of an x-ray system for creating tomographic image data, comprising:

at least one emitter-detector system which, during a scanning period, can determine projection data with a predefined x-ray energy spectrum in each case from a plurality of projection positions and projection directions, a computer system for controlling the at least one emitter-detector system and evaluating determined projection data for reconstructed tomographic image datasets, and a memory for storing computer programs which are executed by the computer system during operation, wherein at least one computer program is stored in the memory, which during operation can execute at least one of the variants of the inventive method described here.

Furthermore an acceleration voltage can be applied to the emitter which determines the maximum energy of the emitted x-ray energy spectrum, and a random generator can be present, through which the switchover of the acceleration voltages is determined.

In addition an acceleration voltage can be present at the emitter which determines the maximum energy of the emitted x-ray energy spectrum, wherein a predetermined temporal random pattern is present which predetermines the switching of the acceleration voltages.

Figure 2:
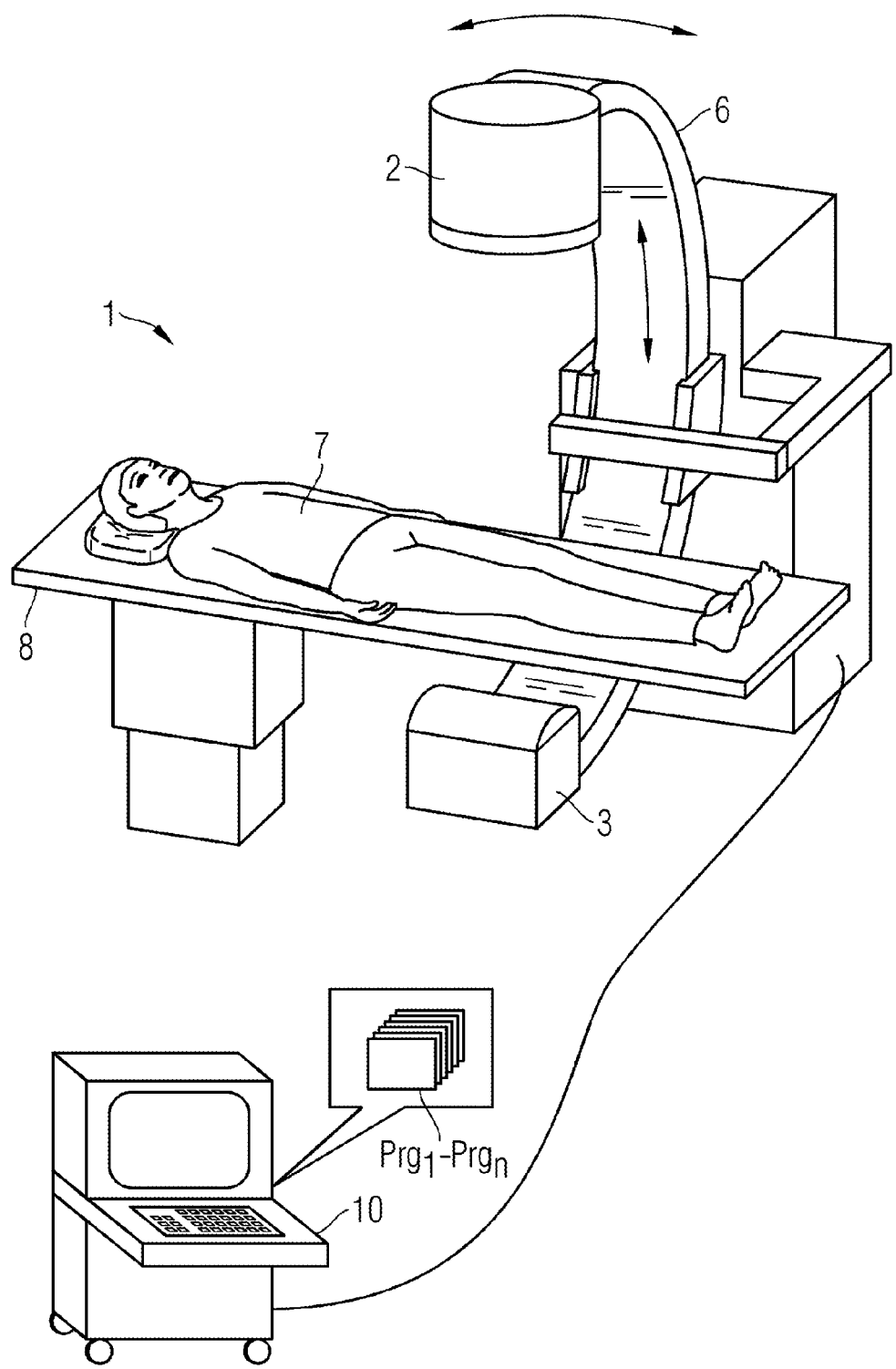
FIG. 2 shows a C-arm system.
Figure 3:
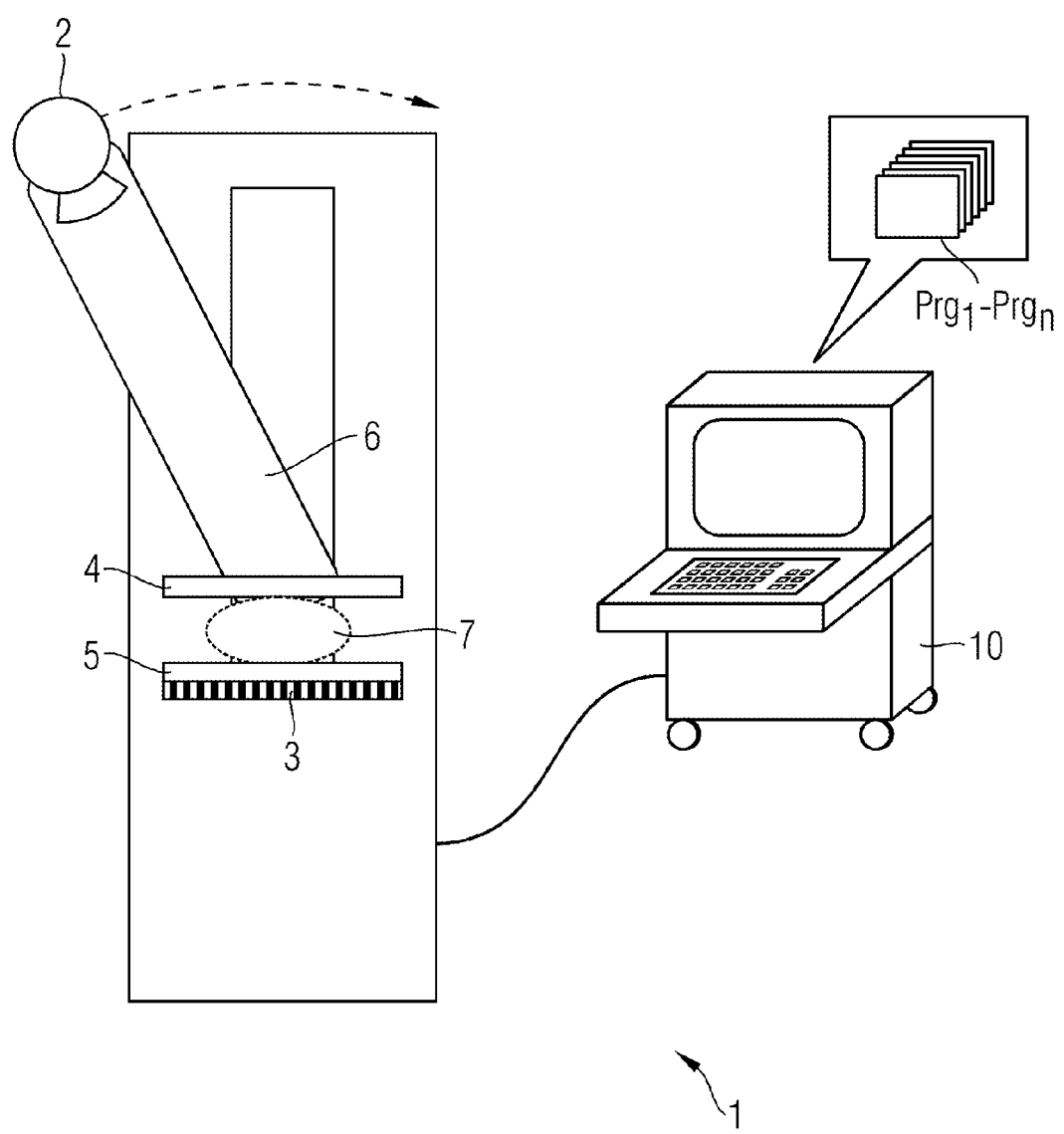
FIG. 3 shows a mammography tomosynthesis system.

FIGS. 1 to 3 show examples of x-ray systems which are equipped for carrying out the inventive method. FIG. 1 shows a single-energy source CT system 1 with a gantry 6 in which an emitter-detector system consisting of an x-ray tube 2 and a detector 3 disposed opposite said tube are disposed rotatably around a system axis 9. For scanning the patient 7 is pushed continuously or sequentially with the aid of the movable patient table 8 through the measurement field in the gantry, while the emitter-detector system rotates for scanning and, in accordance with a random pattern, the tube voltage is switched between at least two predetermined acceleration voltages. The manner of this switchover is explained once more in greater detail below. The system 1 is controlled by a control and processing unit 10, in which computer programs Prg1-Prgn which execute the inventive method during operation are stored in a memory. It is pointed out here that in addition a second emitter-detector system—not explicitly shown here—can be disposed in the gantry without departing from the scope of the invention.

FIG. 2 shows a further example of an inventive x-ray system in the form of a C-arm system 1. This possesses an emitter-detector system disposed on a C-arm 6, consisting of an x-ray tube 2 and a detector 3. For scanning the patient 7 the emitter-detector system 2, 3 is pivoted around the patient with the aid of the C-arm, wherein here too, through a corresponding programming of the control and processing unit 10 during the pivot, a non-regular switchover of the acceleration voltage at the x-ray tube 2 is carried out.

Finally FIG. 3 also shows, as an example of an inventively equipped x-ray system, a mammography tomosynthesis system 1, which likewise has an emitter-detector system, consisting of an x-ray tube 2 located on a movable pivot arm 6 and a detector 3, here in a fixed position. For scanning, the breast of the patient 7 is located between an upper and a lower pressure plate 4 and 5, which insures that the breast is fixed during the scanning. In the scanning the pivot arm 6 is pivoted in an arc around the breast of the patient 7 while, controlled by the control and processing system 10, a switch is made in an inventive manner between two different acceleration voltages and accordingly the readings are performed with different x-ray energies in accordance with a random principle, but with predetermined numerical ratios. To perform the inventive scanning method and the subsequent reconstruction of the image data, as in the previous x-ray systems described, the corresponding programmed control and processing system 10 with its computer programs Prg1-Prgn is also used here.

Figure 4:
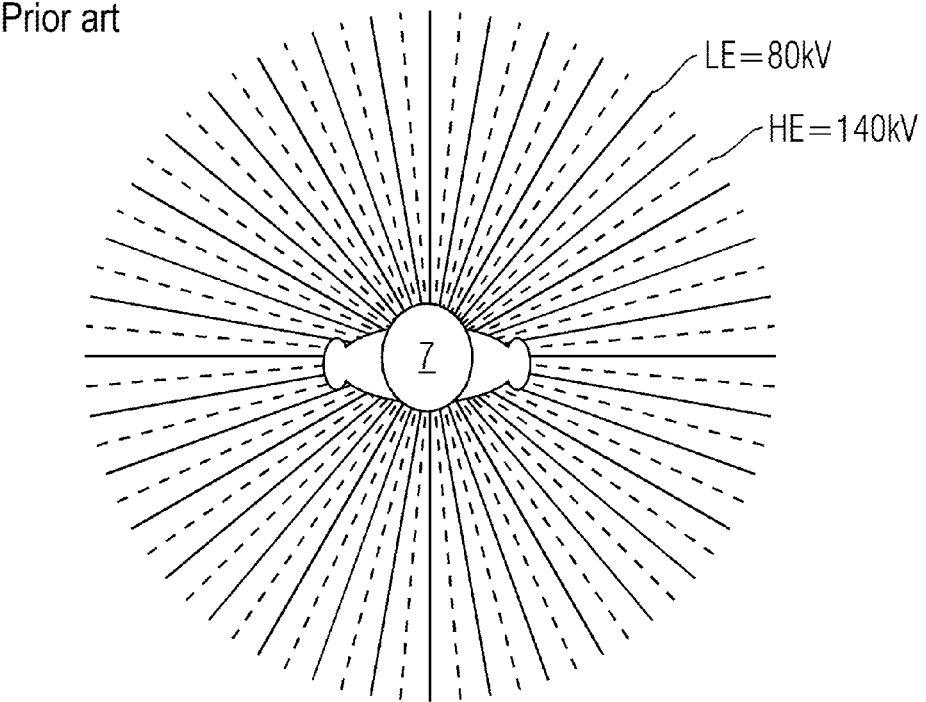
FIG. 4 shows a sampling pattern of a single-energy source and dual-energy source CT system according to the prior art.
Figure 5:
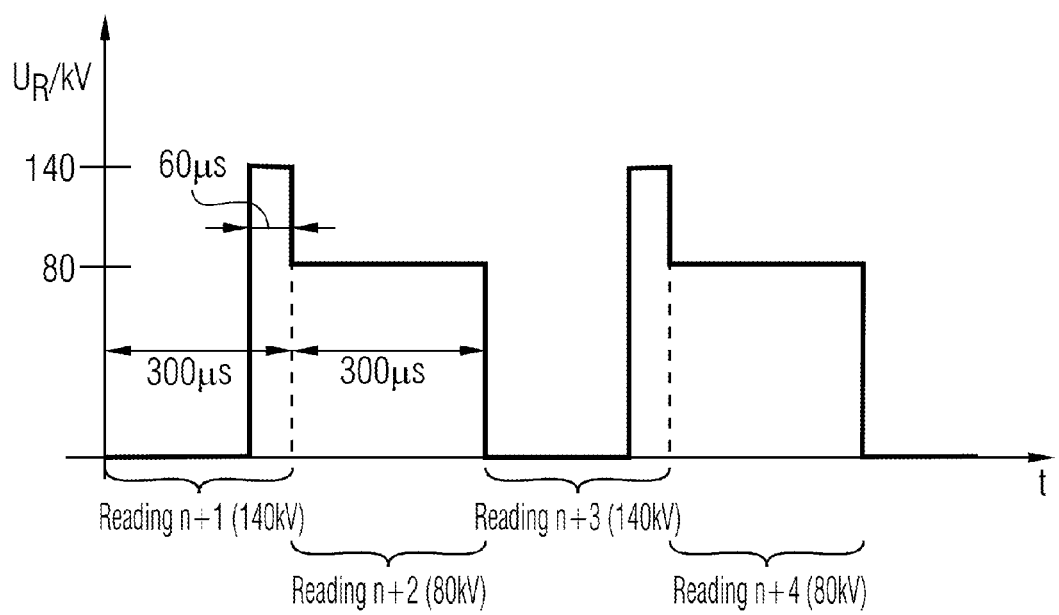
FIG. 5 shows a presentation of the readings of the sampling pattern from FIG. 4.

How an embodiment of the inventive scanning method differs compared to the prior art will be explained on the basis of FIGS. 4 and 5 compared to FIGS. 6 and 7. FIG. 4 describes schematically a circular dual-energy spectrum scanning of the patient 7 with a single-energy source CT system in accordance with a fast-kV-switching method, as is described in publication U.S. Pat. No. 7,209,537. In this case the emitter-detector system, in its rotation around the patient is alternately switched between consecutive readings between two different acceleration voltages. This is clarified in FIG. 4 by the presentation of the central projection directions with higher-energy HE (dashed lines) and lower energy LE (solid lines). The corresponding switchover of the acceleration voltages is illustrated in FIG. 5, wherein it should be noted that the duration of the readings is the same regardless of the acceleration voltage used, but that with higher energy (140 kV) the voltage is only present for a fifth of the total duration of the reading, or the duration of presence of the lower voltage respectively, so that accordingly the dose product of both x-ray energies is at least largely the same during the scanning.

Figure 6:
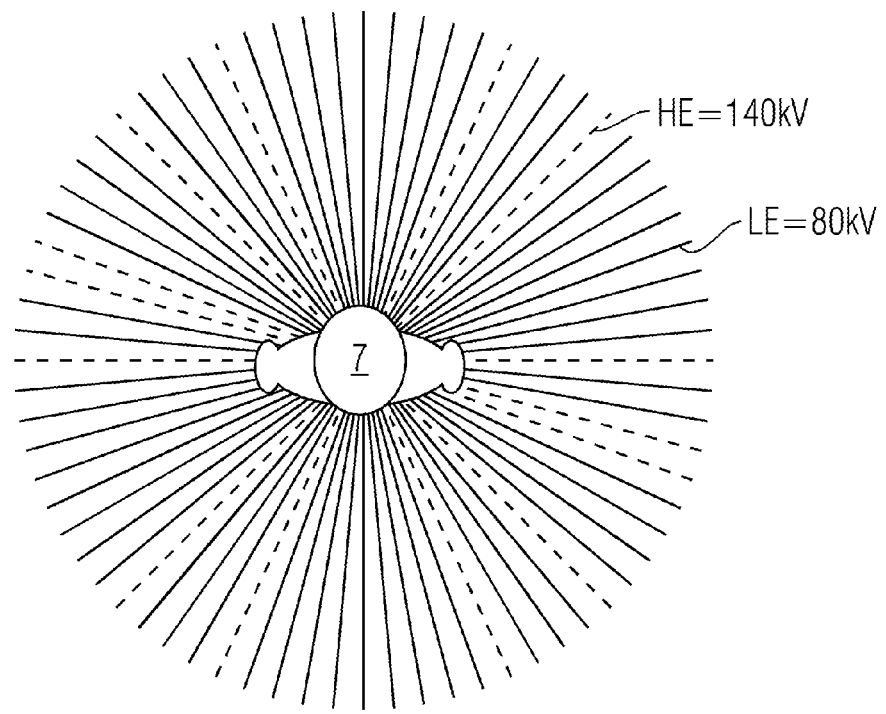
FIG. 6 shows a typical inventive sampling pattern of a single-energy source and dual-energy spectra CT system at 80 kV and 140 kV acceleration voltage.

By contrast with this known scanning method, FIG. 6 shows an inventive dual-energy spectrum scanning of the patient 7 with a single-energy source CT system. As in FIG. 4, here too the central scanning directions with the higher energy (140 kV) are shown by dashed lines and those with the lower energy (80 kV) by solid lines. It should be recognized that during a 180° rotation—such a rotation is shown here—significantly fewer scans with 140 kV occur than with 80 kV. The ratio of the readings of the two spectra lies here at the same tube current IR=constant at 1 to 4 in accordance with the reciprocal ratio of the dose product, assuming an equal irradiation duration and an equal tube current. Since in accordance with the invention the switch-on duration even of the high acceleration voltage corresponds to the full reading time, the overall result is the same dose product for both x-ray energies per pass or per scan respectively.

Figure 7:
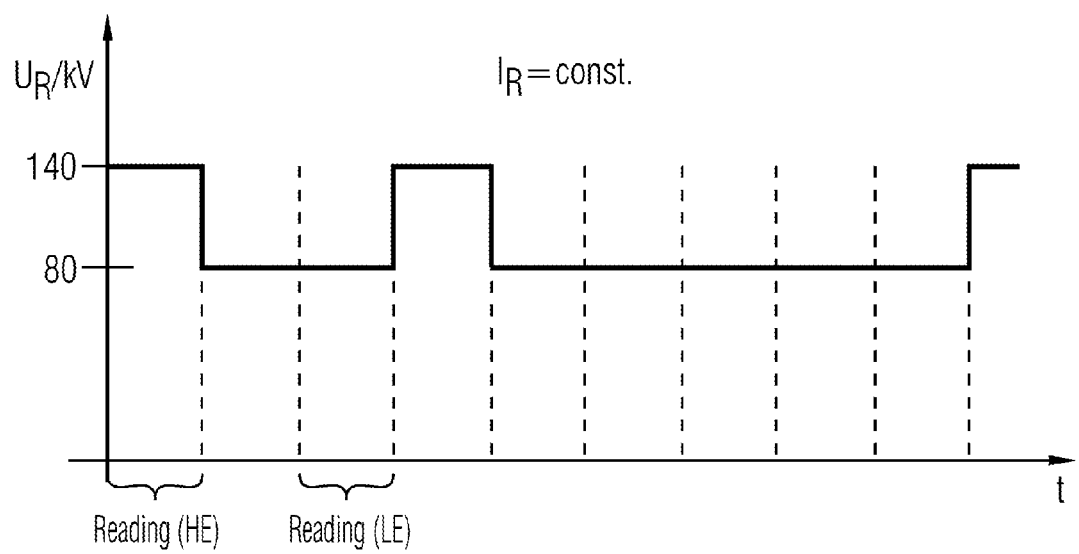
FIG. 7 shows a diagram of the readings of the sampling pattern from FIG. 6.

To this end FIG. 7 shows a section of the curve of the acceleration voltage UR present at the x-ray tube plotted against the readings, the boundaries of which are represented by the dashed lines.

Thus, in an embodiment of the inventive scanning, with the tube current remaining the same, an equal dose product is achieved for the different acceleration voltages used, in that the number of readings per pass or scan is distributed inversely proportional to the ratio of the dose product of the x-ray energies used, wherein in addition no regular pattern or pattern with cyclic repetitions but random patterns complementary to one another are used for the scan, which preferably create a seamless scan.

If scans such as are referred to in technical literature by the term "compressed sensing" are carried out, then from the incomplete or sparsely populated projection data produced, with the aid of the iterative CS reconstruction method or the iterative PICCS reconstruction method, image data for each of the x-ray energy spectra used can be calculated. In such cases the CS reconstruction method is especially suitable if only a few readings (less than 50%) are missing from a complete reading set. The PICCS reconstruction method, in which a previously known approximate image of the scanned examination object (prior image) is required, is to an extent predestined on the other hand if only very sparsely occupied projection data (less than 50% of the complete projection data record) is present.

The subsequent FIGS. 8 to 11 show different variants of the inventive method of a dual-energy spectra and single-energy source scan with subsequent iterative reconstruction, taking into account missing readings for each acceleration voltage used in the scan.

Figure 8:
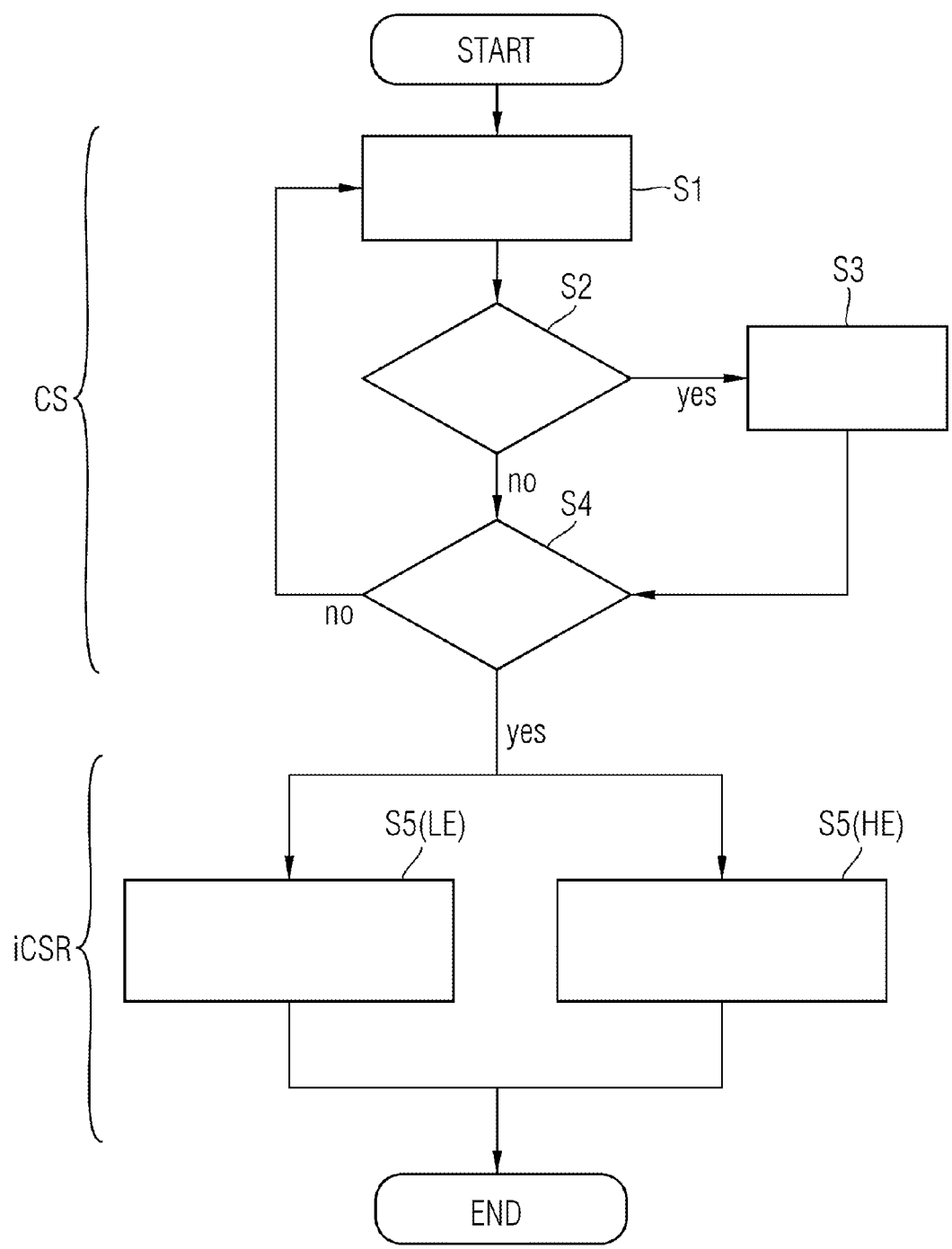
FIG. 8 shows a method scheme for scanning and reconstruction exclusively in accordance with the CS reconstruction method.

A simple first variant of a method sequence in which exclusively an iterative CS method is used for reconstruction is shown in FIG. 8.

After the START, in method step S1 the readings with a single-energy source x-ray system begin, wherein the x-ray system especially describes a CT system, a C-arm system or a mammography tomosynthesis system. This is followed, in method step S2, by the enquiry as to whether kV switching is to be carried out, if "yes", in method step S3, a corresponding switchover of the acceleration voltage is carried out, if "no" the switchover of the acceleration voltage is suppressed and the next reading is taken with the acceleration voltage already present. Here care is taken to ensure that the switchovers on the one hand occur in accordance with the random principle, i.e. no regular patterns occur, and on the other hand the ratio of the readings with the respective acceleration voltage is set inversely proportional to the ratio of the photon flows or to the dose product at the respective tube voltage. In method step S4 it is now decided whether the entire scan processes ended. If this decision is positive then the method goes from scan process CS (compressed sensing) to the iterative reconstruction process iCSR (iterative "compressed sensing" reconstruction).

In the reconstruction process in this variant, which is especially suitable if the number of readings are similar for both acceleration voltages, an iterative CS reconstruction takes place for both energies independently of one another in each case in the method steps S5(LE) for the lower-energy spectrum and S5(HE) for the higher-energy spectrum. At the END the image data thus reconstructed can be output separately or further processing for example by a combination of the image data known per se or the use of a material decomposition method or other known image processing methods based on two different x-ray energy spectra can take place.

Figure 9:
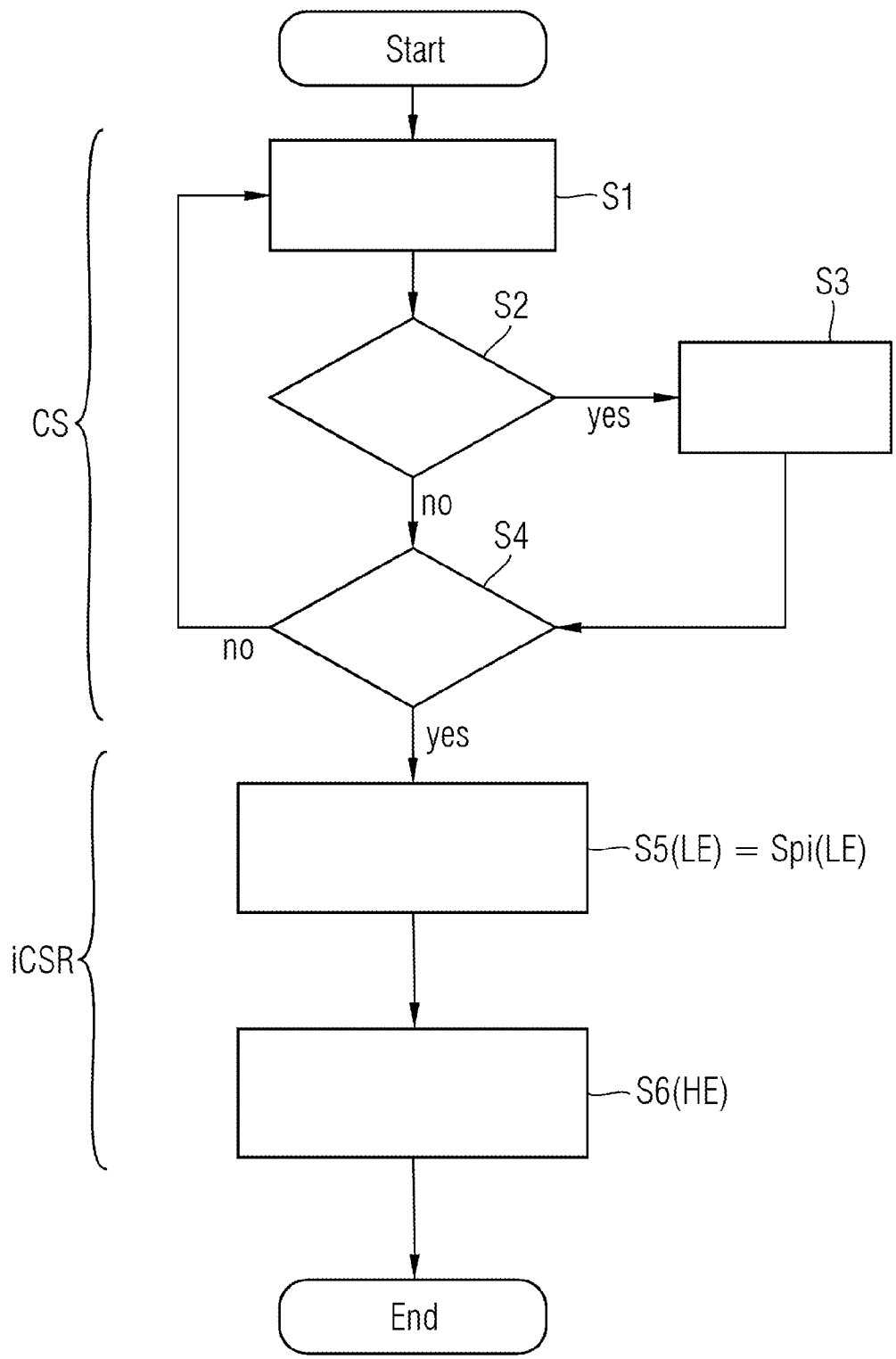
FIG. 9 shows a method scheme for scanning and reconstruction in accordance with the CS reconstruction method for the lower x-ray energy spectrum and in accordance with the combined at CES and PICCS reconstruction method for the higher x-ray energy spectrum.

A further inventive variant of an embodiment of a dual-energy spectra scan with a compressed scanning embodiment CS and subsequent iCSR is shown in FIG. 9. In this variant the assumption is made that the scanning with the lower x-ray energy, e.g. 80 kV, has a relatively high reading density, while the scanning with the higher x-ray energy, e.g. 140 kV, remains relatively sparsely populated, in order overall to deliver a largely equal dose product per complete scan for each x-ray energy. The scanning CS is carried out here with the method steps S1 to S4 in accordance with FIG. 8. Subsequently, in method step S5(LE)=Spi(LE) there is an iterative CS reconstruction with projection data obtained from the lower x-ray energy for creating a tomographic or tomosynthetic image dataset. This image dataset is now used in a further method step S6(HE) as a prior image for the iterative PICCS reconstruction carried out there so that the only sparsely populated readings present can be supplemented accordingly with the higher x-ray energy by prior knowledge on the basis of a prior image and despite this the information only being obtained sparsely in the scanning with the higher x-ray energy, an image arises, which in its image quality and its signal-to-noise ratio corresponds to the already calculated image dataset with the lower energy. As in the method in accordance with FIG. 8, here too the image data reconstructed in this way can be output separately or further processing for example by a combination of the image data known per se or the use of a material decomposition method or other known image processing methods based on two different x-ray energy spectra can take place.

Figure 10:
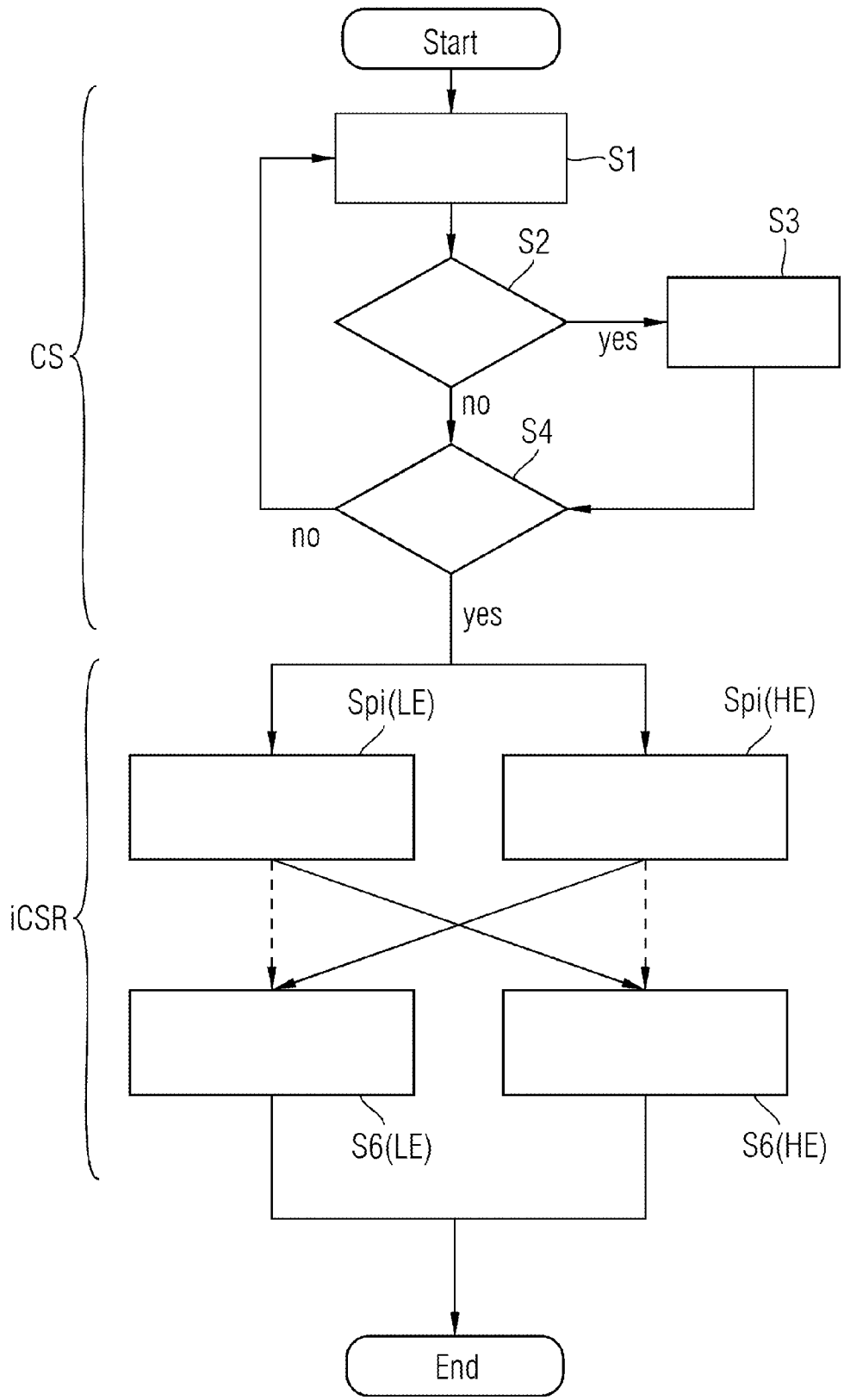
FIG. 10 shows a method scheme for scanning and reconstruction in accordance with a combined alternate CS and PICCS reconstruction method and FIG. 11 shows a method scheme for scanning and reconstruction in accordance with an FBP reconstruction with the sum of the higher and lower-energy attenuation data for a prior image and subsequent CS and/or PICCS reconstruction with the higher and the lower-energy attenuation data.

FIG. 10 shows a third variant embodiment of the inventive method. The scanning CS is undertaken as in FIG. 8, wherein here too two incomplete projection data records are obtained for two different x-ray energy spectra. In the reconstruction section iCSR the two projection data records are initially reconstructed in the method steps Spi(LE) and Spi(HE) in accordance with the iterative CS reconstruction method in each case independently of one another to image datasets of the respective x-ray energy spectrum, which are subsequently used as prior image. Then, in method steps S6(LE) and S6(HE) for each x-ray energy spectrum, an iterative PICCS reconstruction, in which the image dataset reconstructed in each case as prior image of the reconstructed image dataset of the other x-ray energy spectrum in each case reconstructed in accordance with the CS reconstruction method is used. Accordingly the reconstruction profits in each x-ray energy spectrum from the available information from the other x-ray energy spectrum. The image datasets obtained in each case for the two different x-ray energy spectra can then be output, combined or further processed after their production, as already described above.

Figure 11:
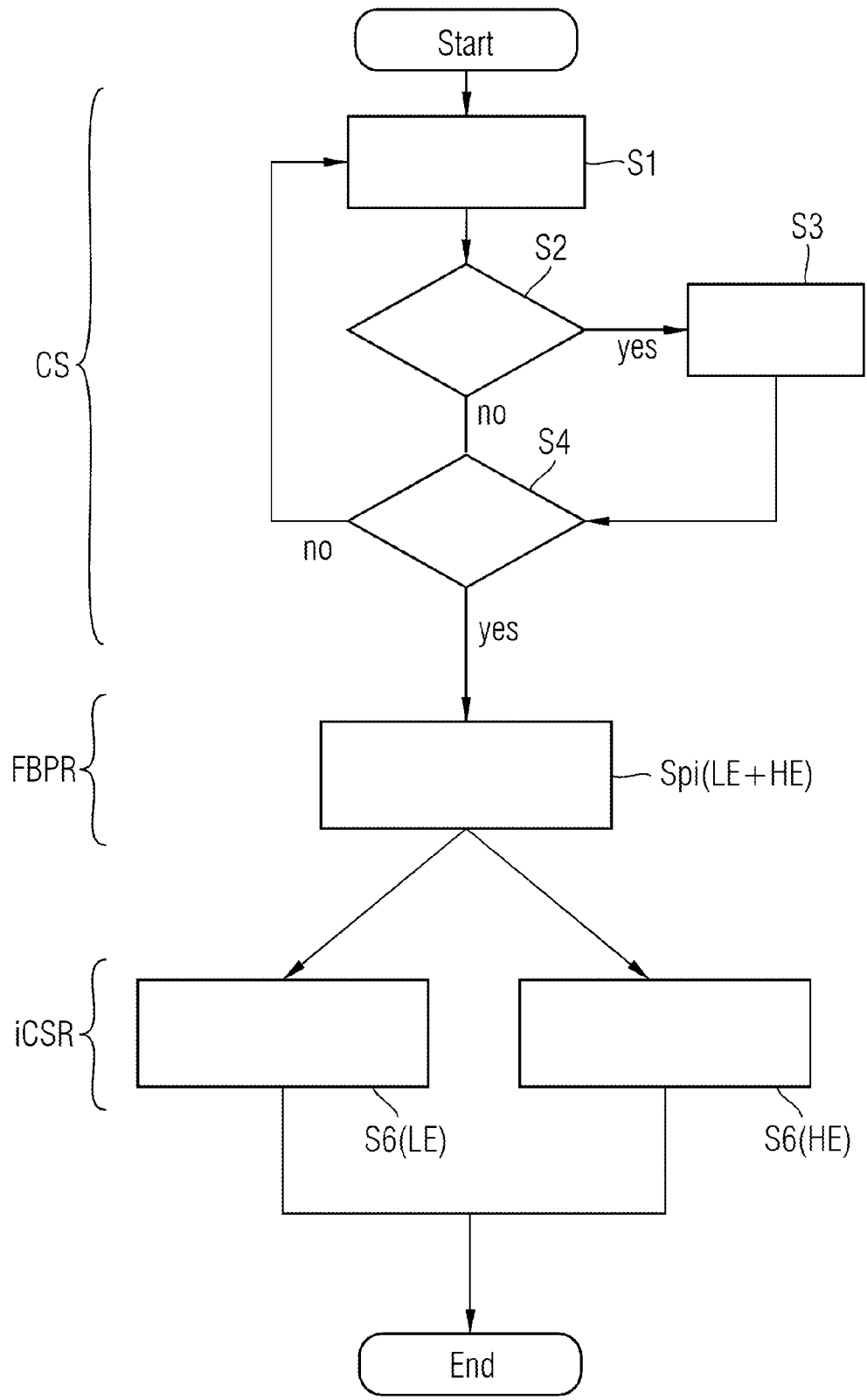

Finally, FIG. 11 shows a fourth variant embodiment of the inventive method. The sampling CS is undertaken as in FIGS. 8 to 10, wherein here once again two incomplete projection datasets are obtained in each case for the different x-ray energy spectra LE and HE. The projection datasets thus obtained are complementary to one another in relation to their readings and produce—if the differences in the scanning x-ray energy spectrum are ignored—one complete projection dataset in total. Such a complete projection dataset can now be reconstructed in the method step Spi(LE+HE) with a standard reconstruction method, here typically a filtered back projection reconstruction FBPR, into a prior image. In the following section iCSR this prior image is used in the method steps S6(LE) and S6(HE) executed in parallel in order to perform a PICCS reconstruction with the projection data of the LE spectrum or the projection data of the HE spectrum.

As an alternative however a combination of the reconstruction types can also be performed, wherein the projection data of the LE spectrum is used for a CS reconstruction, in which the prior image is used as prior knowledge, while the projection data of the HE spectrum is reconstructed by the PICCS reconstruction method. In addition, if the sum of the readings per spectrum does not differ too much, the two projection data records can also be used in each case per se for a CS reconstruction.

Thus a method and an x-ray system for dual-energy spectra CT scanning and image reconstruction of two tomographic image datasets from a higher-energy and a lower-energy x-ray spectrum are proposed in total with the invention wherein, during the scanning, readings are carried out with the different x-ray energy spectra, in that the different x-ray energy spectra are also created at least by different acceleration voltages of the x-ray source and the spatial distribution of the scanning x-rays for each x-ray energy spectrum is undertaken randomly or pseudo-randomly, reconstructions of two tomographic image datasets using the two attenuation datasets are carried out with the attenuation datasets thus obtained in accordance with at least one iterative CS reconstruction method and subsequently a storage and/or output and/or further processing of the reconstructed tomographic image datasets is undertaken.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Although the invention has been illustrated and described in greater detail by the preferred exemplary embodiment, the invention is not restricted by the disclosed examples and other variations therefrom can be derived by the person skilled in the art without departing from the scope of protection of the invention.

What is claimed is:

1. A method for dual-energy spectra CT scanning and image reconstruction of two tomographic image datasets from a relatively higher-energy spectrum and a relatively lower-energy spectrum, comprising:

scanning an examination object with an x-ray source from a plurality of projection positions and projection directions with two different x-ray energy spectra and respectively determining, in each case, an under-sampled attenuation dataset of the examination object for each respective x-ray energy spectrum, wherein the two different x-ray energy spectra are at least each also created by a respectively different acceleration voltage of the x-ray source, and the scanning x-rays, per respective x-ray energy spectrum, are spatially distributed randomly or pseudo-randomly, reconstructing two tomographic image datasets using the two undersampled attenuation datasets in accordance with at least one iterative CS reconstruction method; and at least one of storing, outputting and further processing the reconstructed tomographic image datasets.

2. The method of claim 1, wherein the scanning is undertaken so that a sum of the x-rays of the scanning x-ray energies used produces a regular scanning pattern.

3. The method of claim 2, wherein the scanning is undertaken such that the x-rays of two different x-ray energies are disposed complementarily to one another.

4. The method of claim 1, wherein the acceleration voltage is controlled so that an accumulated sampling time with the relatively higher x-ray energy spectrum is relatively smaller than with the respectively lower x-ray energy spectrum.

5. The method of claim 4, wherein a ratio of the accumulated scanning time with the relatively higher x-ray energy spectrum to the accumulated scanning time with the relatively lower x-ray energy spectrum is defined such that a same overall photon energy flow is deposited, in each case, in the sensor material of the detector by each of the two respective scans.

6. The method of claim 4, wherein a ratio of the scanning time with the respective higher x-ray energy spectrum to the scanning time with the respective lower x-ray energy spectrum is determined so that both scans are performed with a same average dose product, wherein the dose product is respectively calculated with the following formula:

$$D_M = I_R * t * U_R k, \text{ wherein}$$

DM is the average dose product,
$I_R$ is a tube current of the x-ray tube used,
$U_R$ is an acceleration voltage of the x-ray tube,
t is an acceleration time and
k is selected such that a measured signal-to-noise ratio in the detector is the same for the relatively higher and for the relatively lower x-ray energy spectra.

7. The method of claim 6, wherein the tube current is kept constant regardless of the acceleration voltage ($U_R$) present.

8. The method of claim 6, wherein the respective acceleration voltage ($U_R$) selected for a reading, in each case, is present for a same length of time regardless of a size of the acceleration voltage ($U_R$).

9. The method of claim 1, wherein the two tomographic datasets are reconstructed independently of one another and in accordance with a same iterative reconstruction method.

10. The method of claim 1, wherein initially, the reconstruction of the relatively lower-energy tomographic dataset takes place in accordance with the iterative "first" CS reconstruction method and then the reconstruction of the respectively higher-energy tomographic dataset takes place with inclusion of the reconstructed relatively lower-energy tomographic dataset as a prior image in accordance with the PICCS reconstruction method.

11. The method of claim 1, wherein initially, relatively higher and lower-energy tomographic datasets are reconstructed independently of one another and in accordance with a same iterative CS reconstruction method and subsequently, for each x-ray energy spectrum, an iterative PICCS reconstruction method is applied, wherein the tomographic datasets determined by the CS reconstruction are used alternately for the respective other x-ray energy as a prior image in a subsequent iterative PICCS reconstruction method.

12. The method of claim 1, wherein, after the scanning, first an FBP reconstruction to a prior image is carried out using the entire respectively higher and lower-energy attenuation datasets and subsequently, using this prior image, an iterative CS reconstruction is carried out with the attenuation dataset of the respectively lower-energy and the respectively higher-energy x-ray spectrum, in each case.

13. The method of claim 1, wherein, first, after the scanning, an FBP reconstruction to a prior image is carried out using the entire respectively higher-energy and respectively lower-energy attenuation datasets and subsequently, using this prior image with the attenuation dataset of the respectively lower-energy x-ray spectrum, an iterative CS reconstruction and using this prior image with the attenuation dataset of the respectively higher-energy x-ray spectrum, an iterative PICCS reconstruction is carried out.

14. The method of claim 1, wherein a single-energy source CT system is used for carrying out the method.

15. The method of claim 1, wherein a C-arm system is used for carrying out the method.

16. The method of claim 1, wherein a mammography tomosynthesis system is used for carrying out the method.

17. The method of claim 1, wherein a dual-energy source CT system is used for carrying out the method.

18. The method of claim 17, wherein the dual-energy spectra scanning is carried out at each individual emitter-detector system of the dual-energy source CT system.

19. The method of claim 1, wherein the scanning of the examination object is performed as spiral scanning.

20. The method of claim 1, wherein the scanning of the examination object is performed as orbital scanning, preferably as sequential orbital scanning.

21. The method of claim 2, wherein the acceleration voltage is controlled so that an accumulated sampling time with the relatively higher x-ray energy spectrum is relatively smaller than with the respectively lower x-ray energy spectrum.

22. The method of claim 3, wherein the acceleration voltage is controlled so that an accumulated sampling time with the relatively higher x-ray energy spectrum is relatively smaller than with the respectively lower x-ray energy spectrum.

23. The method of claim 8, wherein initially, the reconstruction of the relatively lower-energy tomographic dataset takes place in accordance with the iterative "first" CS reconstruction method and then the reconstruction of the respectively higher-energy tomographic dataset takes place with inclusion of the reconstructed relatively lower-energy tomographic dataset as a prior image in accordance with the PICCS reconstruction method.

24. The method of claim 8, wherein initially, relatively higher and lower-energy tomographic datasets are reconstructed independently of one another and in accordance with a same iterative CS reconstruction method and subsequently, for each x-ray energy spectrum, an iterative PICCS reconstruction method is applied, wherein the tomographic datasets determined by the CS reconstruction are used alternately for the respective other x-ray energy as a prior image in a subsequent iterative PICCS reconstruction method.

25. The method of claim 20, wherein the orbital scanning is sequential orbital scanning.

26. An x-ray system for creating tomographic image data, comprising:
    at least one emitter-detector system which, during a scanning period, is configured to determine projection data with x-ray energy spectra from each of a plurality of projection positions and projection directions;
    a computer system configured to control the at least one emitter-detector system and to evaluate determined projection data to reconstructed tomographic image datasets; and
    a memory configured to store computer programs, executable during operation by the computer system, at least one computer program being stored in the memory, to execute at least the following during operation:
        scanning an examination object with an x-ray source from a plurality of projection positions and projection directions with two different x-ray energy spectra and respectively determining, in each case, an undersampled attenuation dataset of the examination object for each respective x-ray energy spectrum, wherein
            the two different x-ray energy spectra are at least each also created by a respectively different acceleration voltage of the x-ray source, and
            the scanning x-rays, per respective x-ray energy spectrum, are spatially distributed randomly or pseudo-randomly,
        reconstructing two tomographic image datasets using the two undersampled attenuation datasets in accordance with at least one iterative CS reconstruction method; and
        at least one of storing, outputting and further processing the reconstructed tomographic image datasets.

27. The x-ray system for creating tomographic image data of claim 26, wherein an acceleration voltage is applied to the emitter, to determine a maximum energy of the emitted x-ray energy spectrum, and a random generator is present through which alternation of the acceleration voltages is defined concurrently.

28. The x-ray system for creating tomographic image data of claim 26, wherein an acceleration voltage is applied to the emitter, to define a maximum energy of the emitted x-ray energy spectrum, and a temporal random pattern is present to determine a switchover of the acceleration voltages.

* * * * *